United States Patent
DeSilets et al.

(10) Patent No.: US 6,961,606 B2
(45) Date of Patent: *Nov. 1, 2005

(54) MULTIMODALITY MEDICAL IMAGING SYSTEM AND METHOD WITH SEPARABLE DETECTOR DEVICES

(75) Inventors: Mark DeSilets, San Jose, CA (US); Horace H. Hines, San Jose, CA (US); Donald Wellnitz, Fitchburg, WI (US)

(73) Assignee: Koninklijke Philips Electronics N.V., Eindhoven (NL)

(*) Notice: Subject to any disclaimer, the term of this patent is extended or adjusted under 35 U.S.C. 154(b) by 215 days.

This patent is subject to a terminal disclaimer.

(21) Appl. No.: 10/051,590

(22) Filed: Oct. 19, 2001

(65) Prior Publication Data

US 2003/0076925 A1 Apr. 24, 2003

(51) Int. Cl.[7] .................................................. A61B 5/05
(52) U.S. Cl. ...................... 600/415; 600/407; 600/410; 600/425; 606/130; 382/131; 378/205; 128/906; 250/363.04
(58) Field of Search ................................ 600/407, 410, 600/415, 425, 427, 431, 411; 378/205, 21, 62, 63; 606/130; 382/131; 250/363.04; 128/906; 327/507; 324/507

(56) References Cited

U.S. PATENT DOCUMENTS

| | | |
|---|---|---|
| 5,178,146 A | 1/1993 | Giese |
| 5,349,956 A | 9/1994 | Bonutti |
| 5,525,905 A | 6/1996 | Mohapatra et al. |
| 5,562,094 A | 10/1996 | Bonutti |
| 5,713,357 A | 2/1998 | Meulenbrugge et al. |
| 5,851,182 A | 12/1998 | Sahadevan |
| 5,938,613 A * | 8/1999 | Shmulewitz ............. 600/461 |
| 5,960,054 A * | 9/1999 | Freeman et al. ............ 378/4 |
| 6,205,347 B1 | 3/2001 | Morgan et al. |
| 6,275,722 B1 * | 8/2001 | Martin et al. ............. 600/410 |
| 6,302,579 B1 | 10/2001 | Meyer et al. |
| 6,364,526 B2 * | 4/2002 | Ivan et al. ................ 378/198 |
| 6,490,476 B1 * | 12/2002 | Townsend et al. ........ 600/427 |
| 6,591,127 B1 * | 7/2003 | McKinnon ................ 600/411 |
| 6,603,991 B1 | 8/2003 | Karmalawy et al. |
| 6,754,520 B2 * | 6/2004 | DeSilets et al. ........... 600/415 |
| 2002/0032927 A1 | 3/2002 | Dinkler |
| 2003/0058984 A1 * | 3/2003 | Susami et al. ............. 378/19 |
| 2003/0078488 A1 * | 4/2003 | DeSilets et al. ........... 600/407 |
| 2003/0103597 A1 * | 6/2003 | Sklebitz ................... 378/63 |

FOREIGN PATENT DOCUMENTS

| | | |
|---|---|---|
| JP | 5344964 | 12/1993 |
| WO | WO 00/75691 A1 | 12/2000 |

OTHER PUBLICATIONS

U. S. Appl. No. 10/039,796; filed Oct. 19, 2001; Multimodality Medical Imaging System and Method with Patient Handling Assembly; by Mark DeSilets, et al.

U. S. Appl. No. 10/027,843; filed Oct. 19, 2001, Multimodality Medical Imaging System and Method with Intervening Patient Access Area; by Mark DeSilets, et al.

* cited by examiner

Primary Examiner—Brian L. Casler
Assistant Examiner—William Jung
(74) Attorney, Agent, or Firm—Douglas B. McKnight

(57) ABSTRACT

The invention comprises a system and method for creating medical images of a subject patient using a plurality of imaging devices, such as tomographic imaging scanners. The imaging devices each have a bore through which a patient is translated during scanning. The imaging devices can be moved apart to allow greater access to a patient between the bores.

15 Claims, 11 Drawing Sheets

MULTIMODALITY MEDICAL IMAGING SYSTEM AND METHOD WITH SEPARABLE DETECTOR DEVICES

TECHNICAL FIELD

The invention relates to multimodality medical imaging systems for viewing anatomical structures and functions of a patient, such as combined x-ray Computed Tomography (CT) and Positron Emission Tomography (PET) scanners and, more particularly, to separating the scanners to facilitate use of one scanner independently of the other scanner.

BACKGROUND OF THE INVENTION

Tomographic imaging devices or cameras are frequently used to assist in the diagnosis and treatment of a variety of anatomical structures and physiologic functions within the body of a subject patient, while minimizing the need for invasive procedures. Such devices typically utilize scanners that obtain data or information about such structures and functions from the patient at specified, discrete locations along the length of a patient. Using this information, the camera produces a series of images, each depicting a cross-section of the body of the patient, in a plane generally perpendicular to the length of the patient, and at specified points along the length of the patient. Combined, successive images or a substantially continuous spiral image taken along the length of a patient can yield a relatively three-dimensional view of internal organs and tissues, or at least provide a cross-sectional view of bodily structures or functions at various places on the patient. Tomographic cameras are most frequently used to view and treat organs and other tissues within the head, torso and trunk of a patient and, in particular, diagnose and treat such ailments as heart disease, arteriosclerosis, cancer, and the like.

Tomographic imaging cameras are often identified by the "mode" or "modality" of radiation used by their scanners to obtain patient data. Well-known scanner modalities include the X-ray Computed Tomography (CT), Magnetic Resonance Imaging (MRI), Ultra-sound (ULT), Single Photon Emission Computed Tomography (SPECT) and Positron Emission Tomography (PET) scanners. Camera systems which combine two or more different scanners to obtain a greater variety of imaging information from a patient are referred to as "multimodality imaging systems." Conversely, tomographic cameras utilizing the same mode to collect imaging information are referred to as having the same modality.

A tomographic camera utilizes a scanner having an array of radiation detectors forming a ring or bore that surrounds a patient. The scanner gathers information along a plane defined by the detector ring, which intersects the patient substantially perpendicularly to the length of the patient. Other processors and instruments coupled to the scanner form the tomographic image, based on information received from the scanner. To obtain information at successive points along the head, torso and trunk of a patient, the patient is supported horizontally on a patient table that translates or moves the patient horizontally through the bore of a tomographic camera.

It is often desirable to utilize two or more adjacent tomographic scanners of different modalities, in multimodality systems, to obtain a variety of imaging information from a single traverse of a patient through multiple scanner bores. This is highly desirable as a means of increasing efficiency (by completing two or more scans in one operation), increasing the accuracy of indexing, correlating or linking multimodality images to the same location along the length of the patient (by coordinating operation of the scanners to a single, controlled movement of the patient) and reducing the labor costs otherwise associated with separate, multimodality scanning operations.

In general, multimodality systems include a series of scanners, each having a different modality, supported by a single housing. Each scanner obtains different information about the patient, which, when combined, provides a better understanding of the patient. More specifically, multimodality cameras typically include a scanner of anatomical structures of the patient (e.g., CT, MRI and Ultrasound cameras) and a scanner of physiologic functions of the patient (e.g., SPECT and PET cameras). The series of scanners forms a relatively long bore, typically longer than the combined head and torso of taller patients and spanning the entire length of shorter patients. The patient is moved at a relatively slow rate through the lengthy multimodality scanning bore, while imaging information is obtained.

The residence time of a patient within the multimodality scanner bore closure typically is in the range of from less than a minute to as much as an hour or more. During much or all of this time, the patient is isolated from operators of the multimodality scanners and cameras, from caregivers who may need to treat the patient, adjust instruments connected to the patient, or perform interventional applications (i.e., image-guided biopsies and the like), and from caregivers who might otherwise attend to the patient, should the patient become upset or ill from ingested radiopharmaceuticals, and the like. Moreover, the relatively lengthy isolation of the patient within the tight quarters of the bore can cause anxiety, such as claustrophobia, and other discomfort or stress in the patient.

These shortcomings of multimodality cameras make their use less desirable when all modalities of imaging are not required. For example, in the event use of only the first scanner of a multimodality system is needed, such as use of a CT scanner forming the front portion of the scanner bore, the patient will remain within the scanner bore. In that circumstance, the extended length of the bore forming an imaging area for the PET scanner is unused. Nevertheless, should interventional applications or other procedure require direct access to a patient by a caregiver, additional time and effort will be required to extend or withdraw the patient from either end of the multimodality scanner bore. Moreover, unnecessary levels of patient discomfort, stress and anxiety result.

Accordingly, there is a need for a multimodality tomographic imaging system that allows use of less than all scanners and corresponding adjustment of the length of the scanner bore, to provide more immediate patient access and to reduce the time and effort needed to handle or attend to the patient.

SUMMARY OF THE INVENTION

The invention comprises a system and method for creating medical images of a subject patient using a plurality of imaging devices, such as tomographic imaging scanners. The imaging devices each have a bore through which a patient is translated during scanning. The imaging devices can be moved apart to allow greater access to a patient between the bores.

In one aspect of the invention, open area is formed between the imaging devices along the path of the patient, through which a caregiver can attain line-of-sight visual contact with or other access to the patient. The access area size is variable by adjustment of the distance separating the imaging devices.

In another aspect of the invention, a mechanism aligns the bores of the imaging devices to allow multimodality scanning.

BRIEF DESCRIPTION OF THE DRAWINGS

For a more complete understanding of the present invention, and the advantages thereof, reference is now made to the following description taken in conjunction with the accompanying drawings, in which.

DETAILED DESCRIPTION

Figure 1:
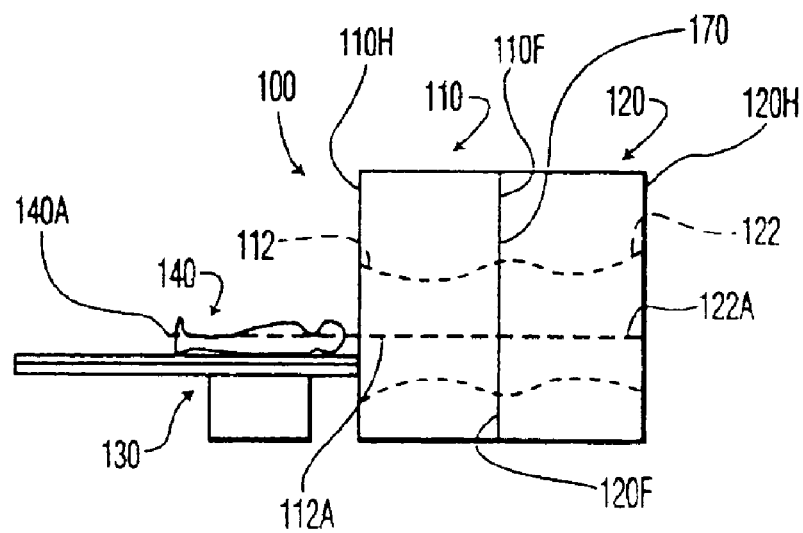
FIG. 1 is a schematic side view of a multimodality medical imaging system incorporating the present invention, with the imaging devices in an adjoining position.

Shown in FIG. 1 is a multimodality medical imaging system scanner assembly 100, having first and second imaging devices 110 and 120. In the embodiment shown, each of the imaging devices 110 and 120 comprise at least a scanner having a modality of operation, and may also include associated scanner support structure and associated electronics. Further, in the embodiment shown, each of the imaging devices 110 and 120 includes a scanner opening or bore 112 and 122 (shown by broken lines), respectively, through which a patient table 130 extends and translates a subject patient 140 during a scanning operation. It will be apparent that imaging devices 110 and 120 may alternatively utilize scanners or detectors that obtain information about the patient 140 without being configured to form a bore, such as a partial closure, an arrangement of one or more planar detectors and other configurations capable of obtaining patient information. Moreover, it will be apparent that while scanner bores 110 and 120 are preferably circular, other configurations capable of obtaining imaging information may alternatively be utilized.

The patient table 130 serves as a patient support structure that also coordinates movement of the patient 140 with respect to operation of the scanners of the imaging devices 110 and 120, to obtain patient imaging information at one or more desired locations along the length of the patient 140. It will be apparent that a variety of available conventional patient table 130 designs would be suitable for these purposes. It will be apparent that the patient table 130 may be designed or operated to extend the patient 140 past the scanners of the imaging devices 110 and 120 in a variety of methods, such as at a continuous rate, at variable rates, in incremental displacements or a combination of such methods, as may be desired or suitable for the scanning operation to be conducted.

Alternatively, instead of the patient table 130, the present invention may utilize the patient handling assembly more fully disclosed in co-pending U.S. application Ser. No. 10/027,843, filed on Oct. 19, 2001, entitled "Multimodality Medical Imaging System and Method With Patient Handling Assembly" and naming as inventors Mark DeSilets, Timothy Buskard, Joseph Carter, Jacco Eerden and Donald Wellnitz. The content of that application is incorporated herein by reference for all purposes.

The imaging devices 110 and 120 acquire, through their scanners, information from the patient 140 sufficient to form tomographic images of the patient. Each of the imaging devices 110 and 120 is coupled to one or more conventional tomographic imaging processor(s), utilizing conventional imaging software to form images from information received from the imaging devices 110 and 120.

Preferably, the imaging devices 110 and 120 cooperate to obtain patient information through different modalities, to provide anatomical structure images and physiologic function images of the patient 140. More specifically, imaging device 110 is preferably a CT scanner that utilizes X-rays as the mode of obtaining data from which images depicting the internal structure of the patient 140 are formed. On the other hand, imaging device 120 is preferably a PET scanner that utilizes positron emissions originating from a radiopharmaceutical ingested by the patient as the mode of acquiring data from which images depicting primarily metabolic physiological functions within the patient 140 are formed. During operation, the entire body of the patient 140 is passed through the bores 112 and 122 of the respective imaging devices 110 and 120, and their respective scanners, so that a collection of one or more images are obtained from each scanner. When scanning is complete, the patient is retracted in the opposite horizontal direction by the patient table 130, typically at a faster rate than during the scanning operation, to withdraw the patient 140 from the scanner assembly 100, to the starting position at the beginning of the scanning procedure.

Figure 1A:
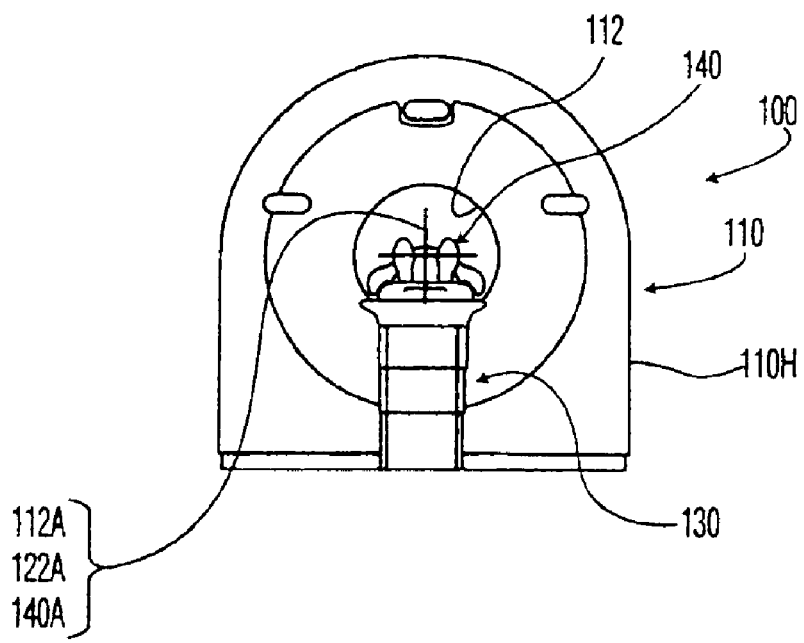
FIG. 1A is a schematic front view a multimodality medical imaging system of FIG. 1.

Referring now to both FIGS. 1 and 1A, the scanner bores 112 and 122 of the imaging devices 110 and 120 are substantially circular, thus surrounding the patient during imaging scanning operations. The axes 112A and 122A of the respective circular openings of each of the bores 112 and 122 are aligned with each other and are preferably aligned with or at least substantially parallel to the path of travel of the patient 140 on the patient table 130. This allows the patient table 130 to translate the patient 140 through the imaging devices 110 and 120 in one substantially continuous pass. Preferably, the center line of the patient 140 is substantially aligned with or at least substantially parallel to the axes 112A and 122A of the detector bores 112 and 122 by adjusting the height of the patient table 130 and the alignment of the table 130 with the bores 112 and 122.

Figure 2:
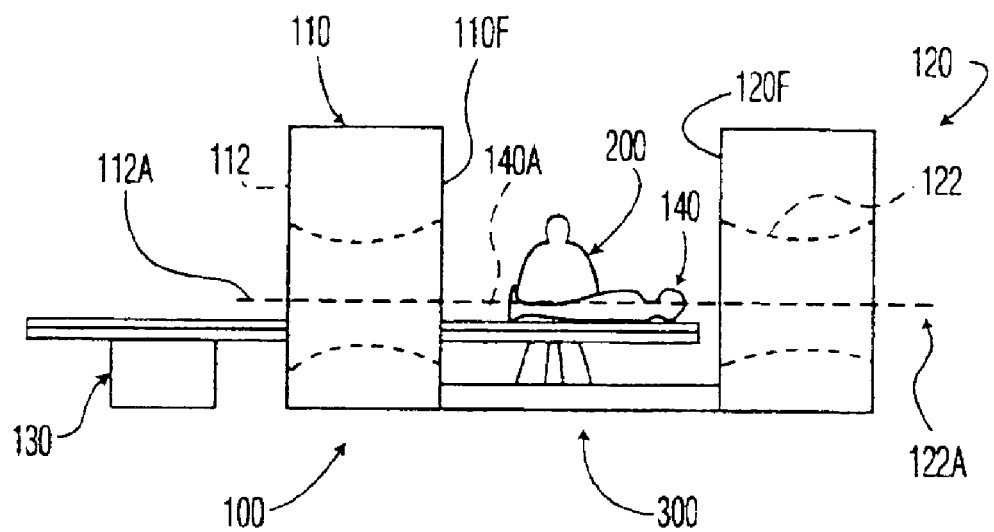
FIG. 2 is a schematic side view of the multimodality medical imaging system of FIG. 1, with the imaging devices in a separated position.

Referring to FIGS. 1 and 2, the imaging devices 110 and 120 are each supported within separate housing portions 110H and 120H, each of which are preferably formed from painted sheet metal and are electrically isolated from internal conductors. Alternatively, the housing portions 110H and 120H are formed from fiberglass or other non-conductive material. The housing portions 110H and 120H are each preferably formed in a unitary construction, and are adapted to be secured together in an adjoining position shown in FIG. 1, at opposing faces 110F and 120F, respectively. Housing portions 110H and 120H contain and support imaging devices 110 and 120, respectively. The opposing faces of the two housing portions 110H and 120H abut and are secured together along seam line 170 in the adjoining position, below the level of the bores 112 and 122 of the imaging devices 110 and 120.

The multimodality medical imaging system scanner assembly 100 includes an actuating mechanism 300 for positioning the housing portions 110H and 120H between adjoining and separate positions, as well as virtually any intervening position along a range of approximately 1.5 meters. It will be apparent that actuating mechanism 300 may alternatively be configured for shorter or longer ranges of motion, as desired. The actuating mechanism 300 actuates the rear imaging device 120 linearly and substantially along the aligned axes 112A and 122A of the housing portions 110H and 12H. The actuating mechanism 300 may employ a variety of mechanisms, such as a single or stacked set of ball or lead screws, cylinders, gears or the like, powered hydraulically, pneumatically electrically or by other desired power source.

FIGS. 1 and 2 show that the rearward housing portion 120 is driven, while the front housing portion 110 remains fixed, anchored to the underlying support surface, thereby allowing the patient table 130 to remain relatively stationary. However, it will be understood that actuating mechanism could alternatively adjust to position of both of housing portions 110H and 120H or only housing portion 110H, if desired. When in the adjoining position bores 112 and 122 of imaging devices 110 and 120 in maintained in relatively fixed positions, by the abutting housing faces 110F and 120F or by a suitable alignment mechanism. A seam line 170 identifies the contact surfaces of the abutting housing faces 110F and 120F.

As is shown in FIG. 2, separation of the imaging devices 110 and 120 shortens the length of the bore of the medical imaging scanner assembly 100 and allows a caregiver 200 to have direct access to those portions of the patient 140 extending from the bore. When the assembly 100 is utilized in a singly modality, such as when use of only scanner 110 is desired, the actuating mechanism separates imaging devices 110 and 129, preferably prior to scanning. The assembly 100 thus operates similarly to a single mode scanner, without the inconvenience of a lengthy and partially unused bore that would otherwise interfere with access to the patient 140. Prior to use of the assembly 100 as a multimodality scanner, the imaging devices are 110 and 120 actuated into the closed position. In the closed position, with their respective bores 112 and 122 in held axial alignment and in fixed positions relative to each other, to facilitate image registration of the image information obtained by the imaging devices 110 and 120.

Figure 3:
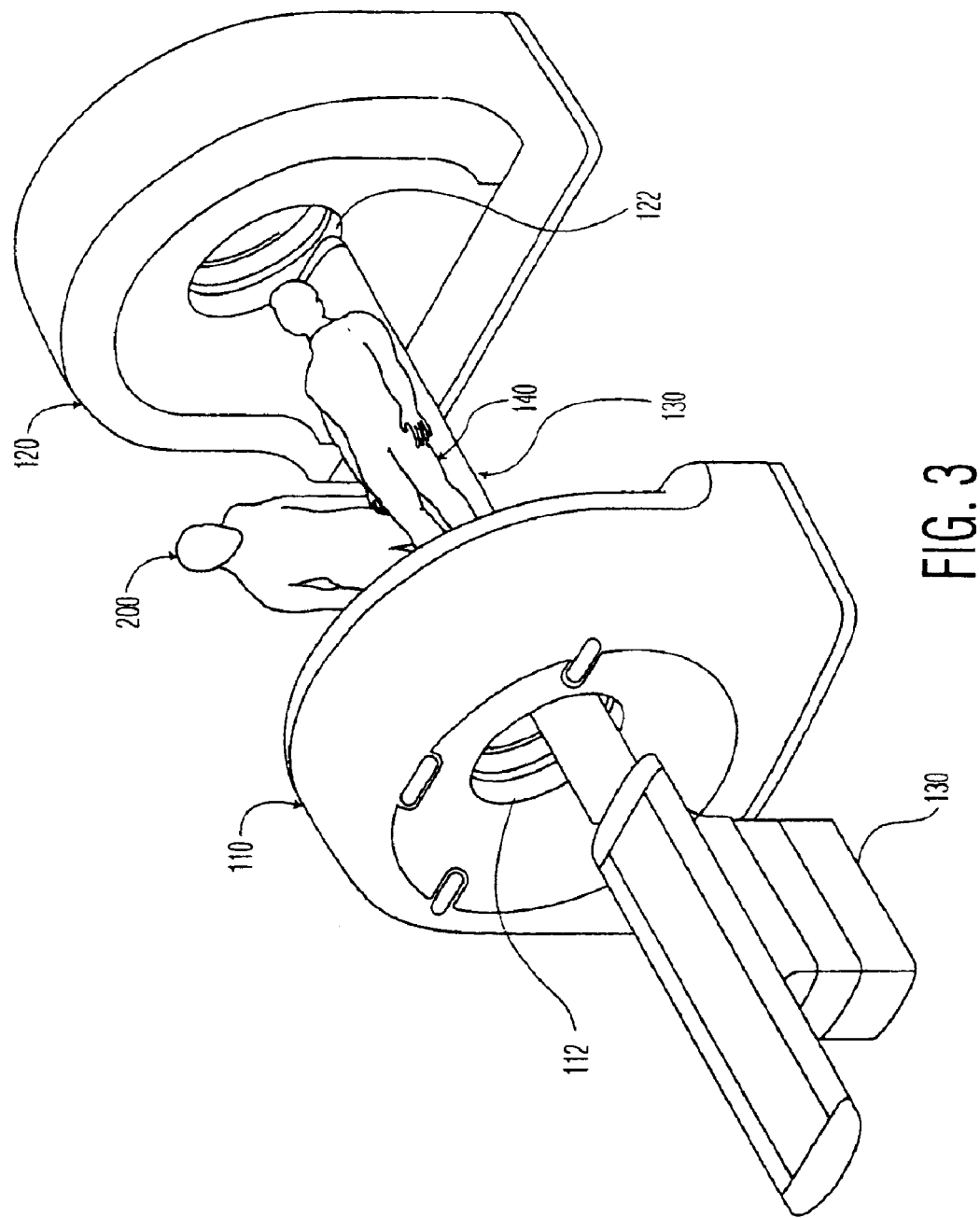
FIG. 3 is a perspective view of a preferred embodiment of a multimodality medical imaging system incorporating the present invention, with the imaging devices in separate positions, similar to the positions illustrated in FIG. 2.
Figure 4:
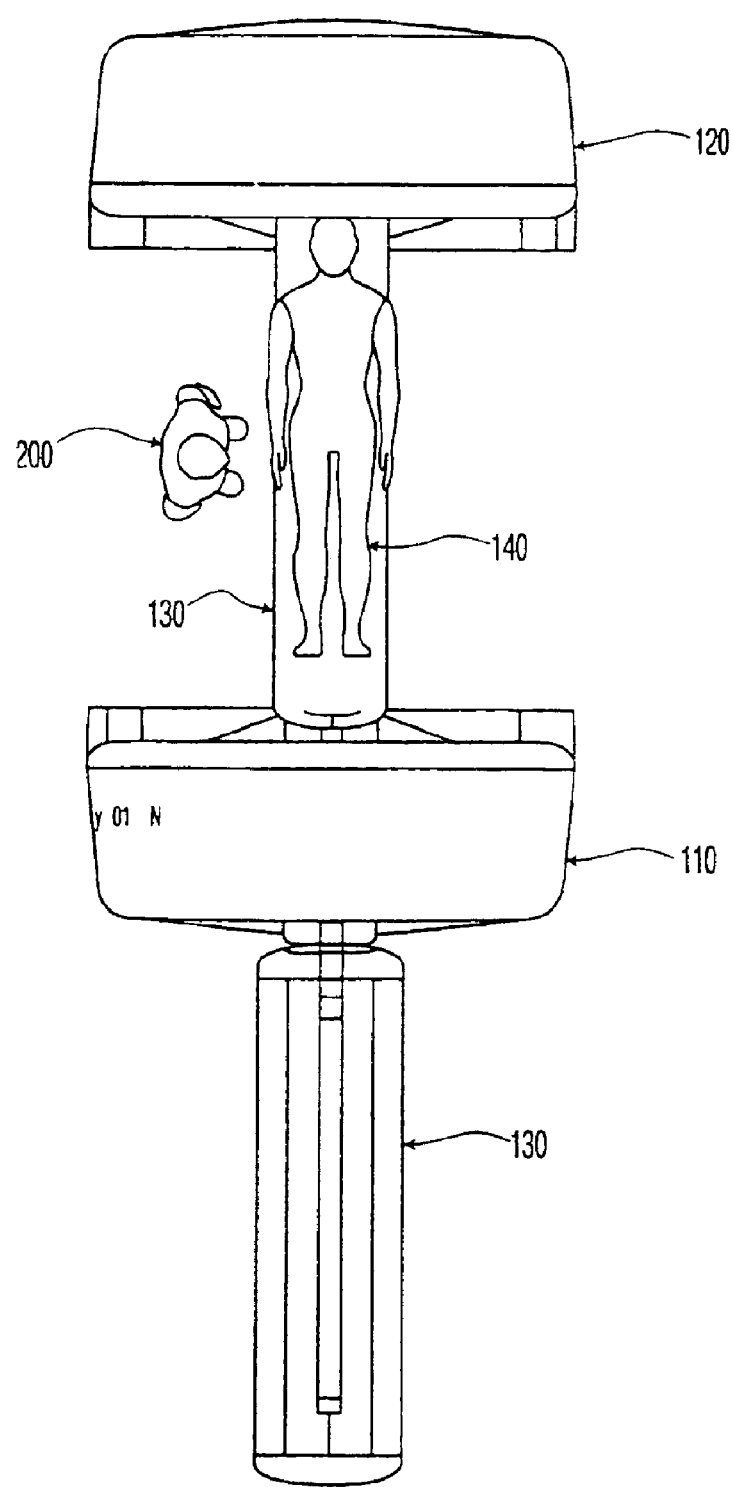
FIG. 4 is a top view of the system shown in FIGS. 3 and 4, with the imaging devices in separate positions.
Figure 5:
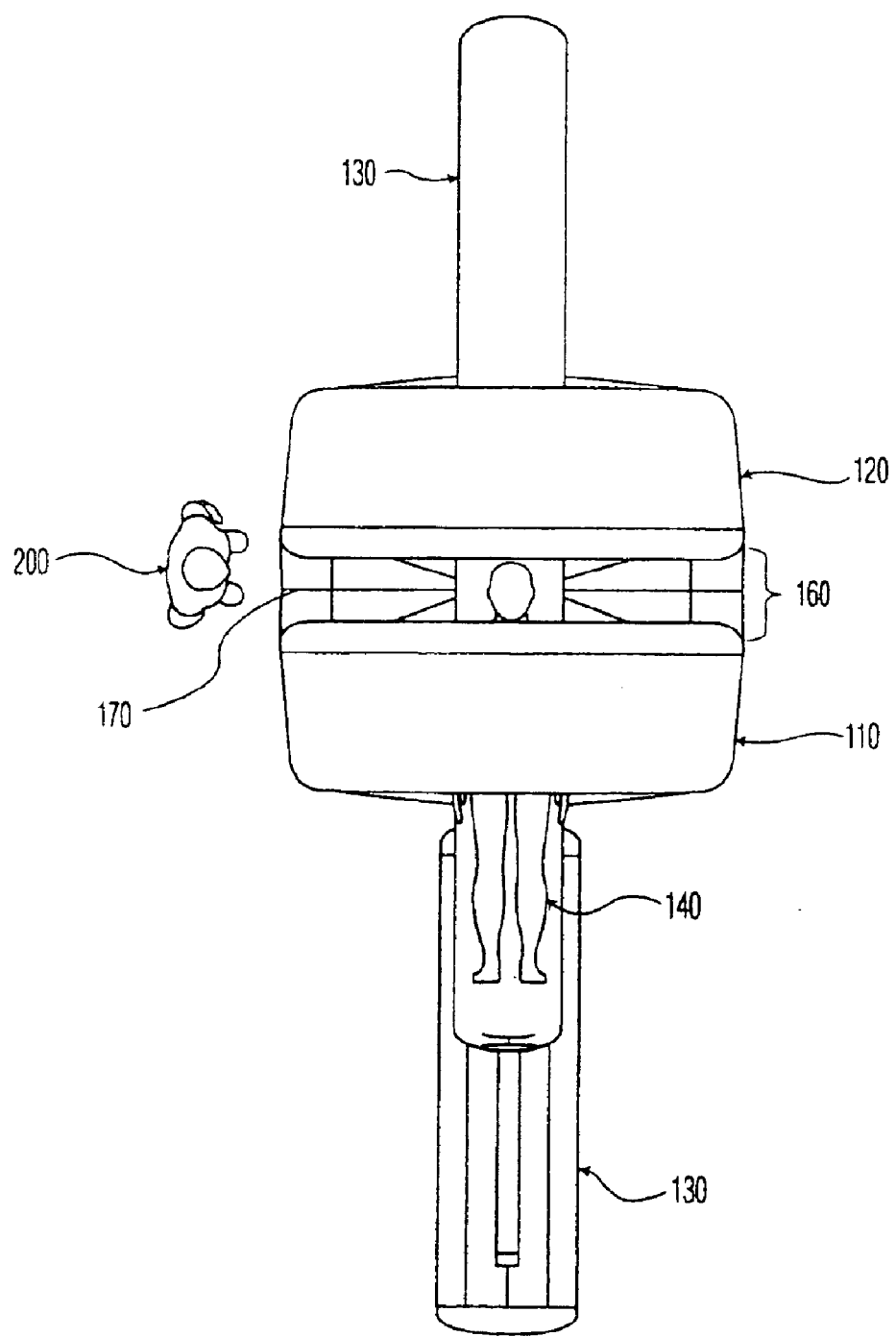
FIG. 5 is a side top view of a the embodiment shown in FIG. 3, with the imaging devices in an adjoining position.

FIGS. 3, 4 and 5 illustrate an embodiment in which an access area 160 is formed by the separation of the imaging devices 110 and 120, when the imaging devices 110 and 120 are in the closed position. In this configuration, the abutting housing faces 110F and 120F extend below the access area 160. FIGS. 3 and 4 illustrates that the caregiver 200 can have access to the entire length of the patient 140. This is accomplished by configuring the actuating mechanism 300 (not shown in FIGS. 3, 4 and 5) to separate the imaging devices 110 and 120 by as much or more than the entire length of the patient 140. Such separation allows unfettered access to virtually every portion of the patient extending between the imaging devices 110 and 120, including the entire length of the patient 140. FIG. 5 illustrates the relative position of the access area 160, patient 140 and caregiver 200, when the imaging devices 110 and 120 are actuated into the closed position, with the head of the patient 140 extending from the CT scanner of imaging device 110. While the caregiver 200 is shown to be an individual, it will be apparent that the term "caregiver" includes any means of providing monitoring, diagnostic treatment, comfort or other care services to the patient 140, such as by use of robotics or other equipment.

The formation of access area 160 is disclosed in co-pending U.S. patent application Ser. No. 10/027,843, entitled "Multimodality Medical Imaging System and Method With Intervening Patient Access Area", naming as inventors Mark DeSilets, Jacco Eerden and Horace H. Hines, filed on Oct. 19, 2001. The content of that application is incorporated herein by reference for all purposes. Access area 160 allows a caregiver 200 to have access to the patient 140 as the patient table 130 translates the patient 140 from the CT scanner 110 to the PET scannner 120 during imaging operations, when the housing portions 110H and 120H are in the closed position.

Maintaining the imaging devices 110 and 120 in fixed relation to each other and in axial alignment when the assembly 100 is in the closed position allows images created from data the scanners separately obtain to be registered correlated, indexed or linked in relation to each other. This is accomplished using information indicating the position of the patient 140 on the patient table 130. More specifically, the patient table 130 includes means for detecting the displacement and position of the patient relative to the multimode scanners of the imaging devices 110 and 120. This information can be used in combination with information indicating the fixed distance separating the scanning planes of the imaging devices 110 and 120 to register, correlate, pair or link the images from each of the devices 110 and 120 to a particular location or point on the patient 140. Each tomographic image obtained from imaging device 110 may thus be paired with or indexed to a corresponding tomographic image obtained from detector 120 with reference to substantially the same location along the length of the patient 140.

Figure 6:
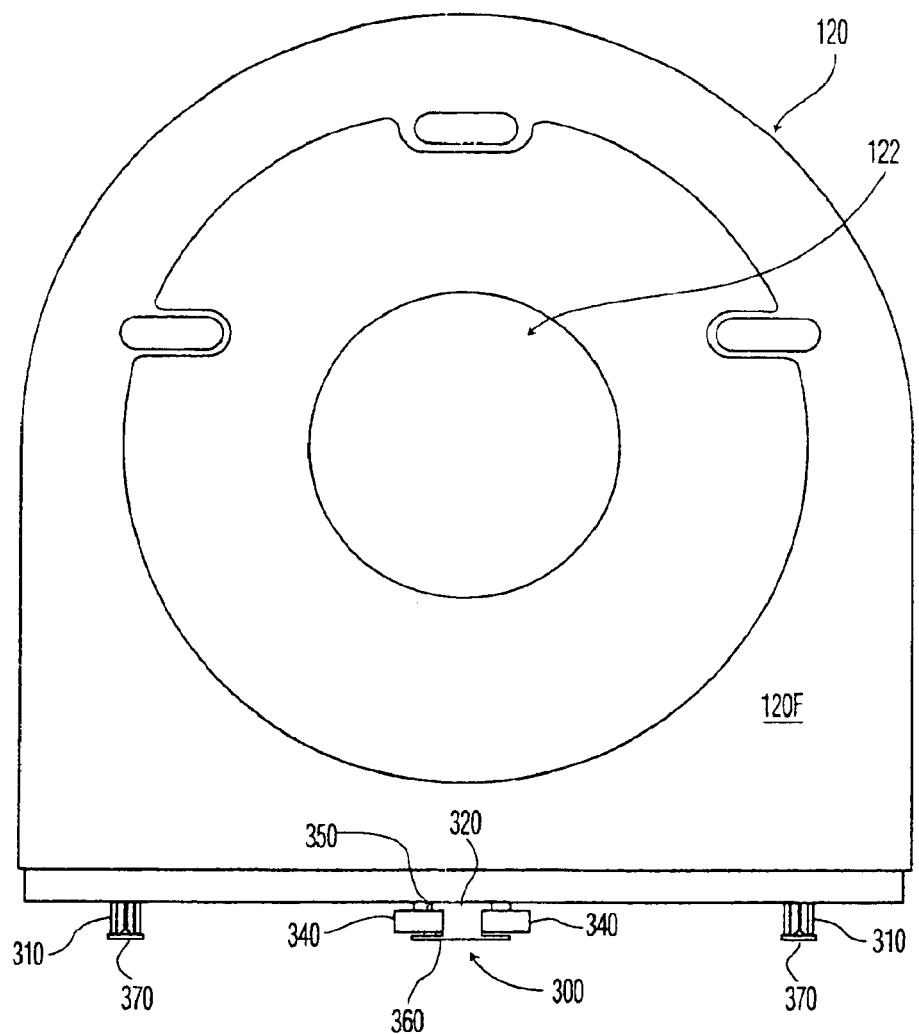
FIG. 6 is a front view of an imaging device and associated mechanism for actuating the device to move between adjoining and separated positions.
Figure 7:
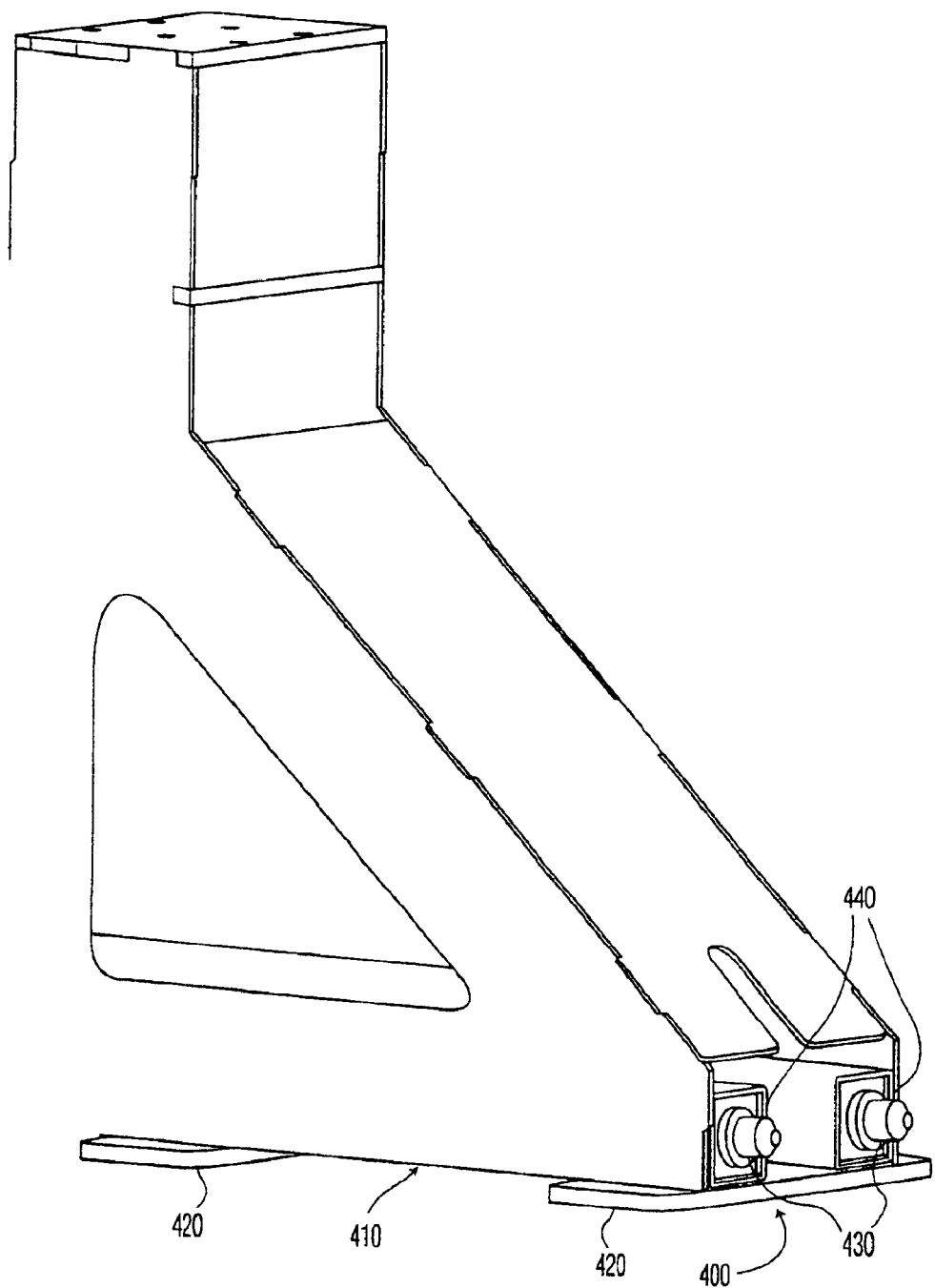
FIG. 7 is a partial perspective view of an alignment and patient table vertical actuating assembly of an imaging device.
Figure 8:
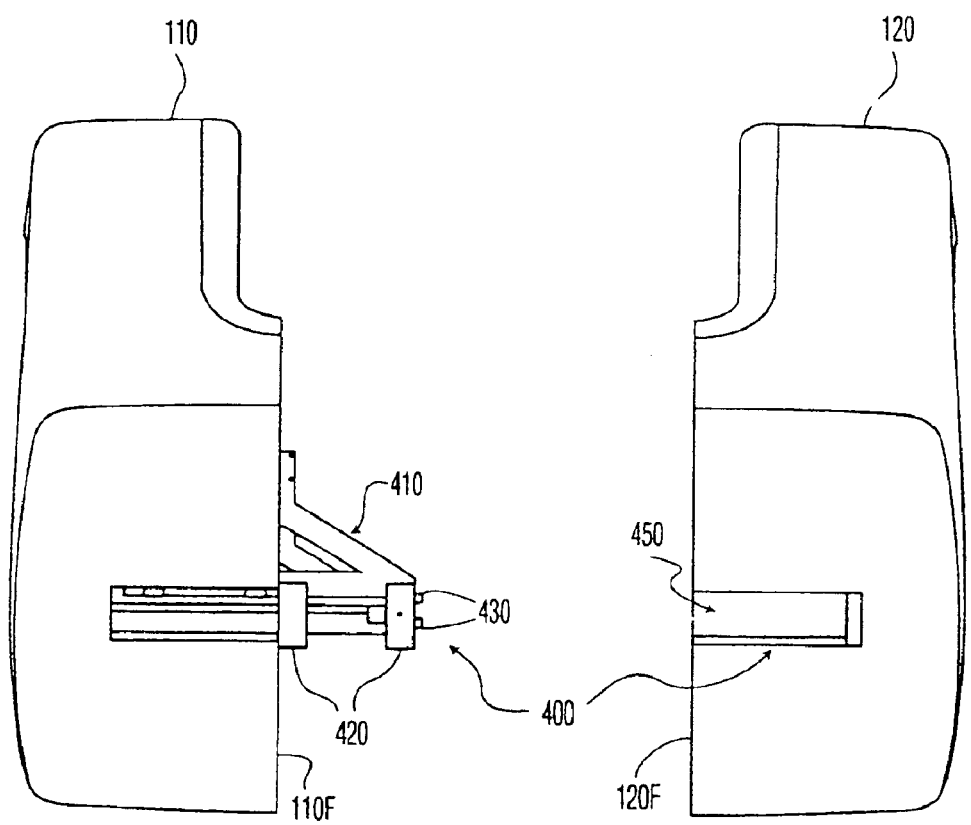
FIG. 8 is a perspective view of two imaging devices taken from below the devices, illustrating the relative position of the alignment and vertical actuating structure shown in FIG. 7.
Figure 9:
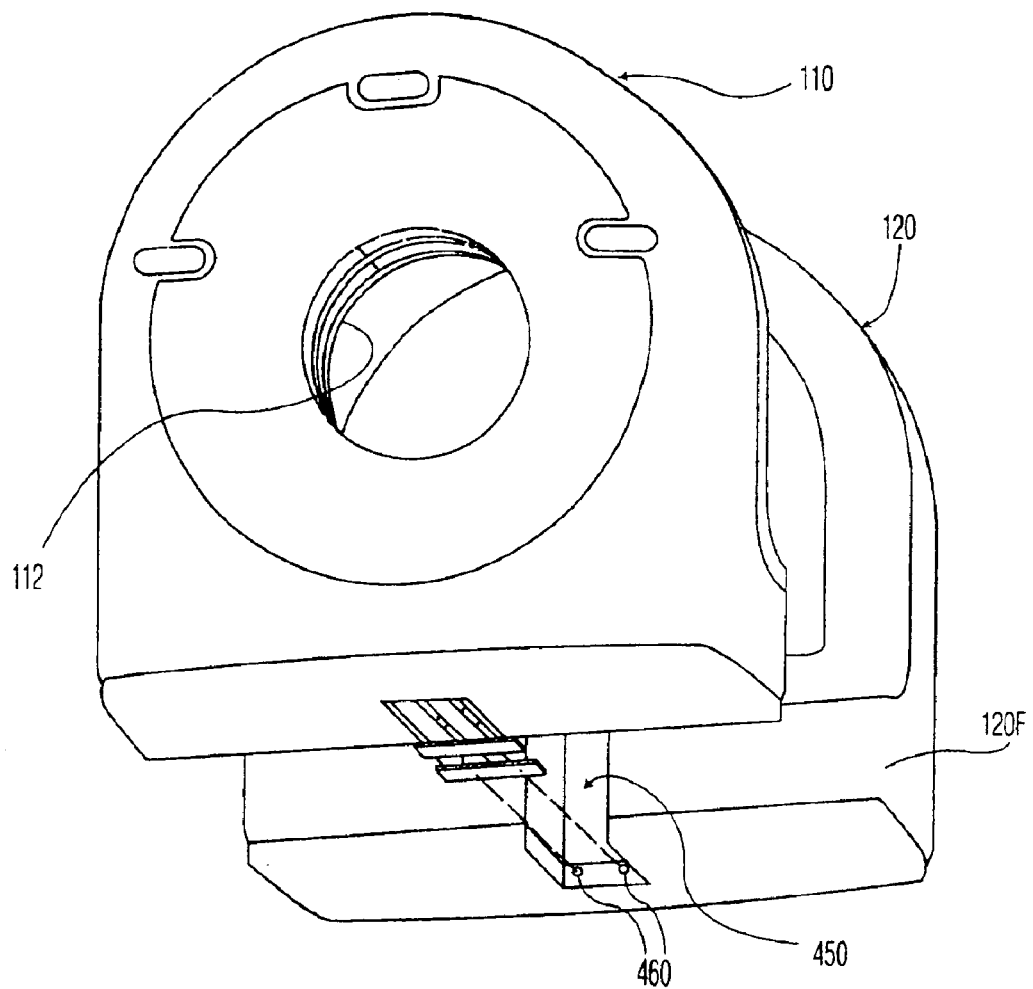
FIG. 9 is a perspective view of two imaging devices taken from below the devices, illustrating additional structure for aligning the devices in an adjoining position.
Figure 9A:
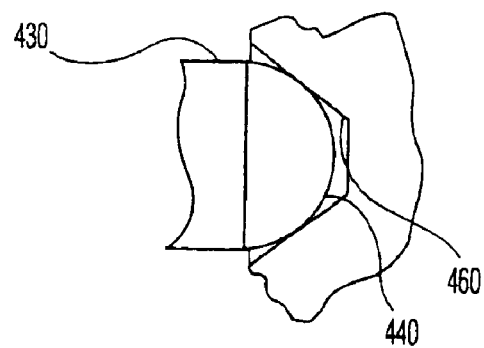
FIG. 9A is a detailed drawing of the a portion of the alignment structure shown in FIGS. 7–9.

Referring now to FIG. 6, shown is a front view of the imaging device 120, supported for movement by four support wheels 310 (only the front two wheels shown), and an associated actuating mechanism 300 for driving the imaging device into engagement with and away from the imaging device 120. The actuating mechanism 300 extends below the imaging device 120 and comprises a drive beam 320 secured to an underlying support surface and drive wheels 340 frictionally engaging and driving along opposite sides of the drive beam 300. The drive beam is substantially aligned with the axes 112A and 122A or the bores 112 and 122. The drive beam 340 includes upper and lower flanges 350 and 360, respectively, forming channels for guiding the drive wheels 340. Preferably, a pair of drive wheels 340 engage and are sufficiently spaced along each of the lateral surfaces of the drive beam 320, to maintain the bore 122 of the imaging device 120 in alignment with the bore axes 112A and 122A. The drive wheels 340 are preferably actuated by electrical motors (not shown) or other suitable power source. The support wheels 310 run on stainless steel wear plates 370 secured to the underlying surface and extending along the path of travel of the support wheels 310.

FIGS. 7, 8, 9, and 9A illustrate a preferred alignment mechanism 400 for laterally and axially aligning the imaging devices 110 and 120 when in the closed position. For clarity, the actuating mechanism 300 and the support wheels of the imaging device 120 are not shown. The alignment mechanism 400 comprises a support frame 410 secured to and extending rearwardly from the front imaging device 100. The support frame 410 is secured by a pair of anchor flanges 420 to the underlying support surface against longitudinal and lateral movement. Secured to and extending rearwardly from the support frame 410 are a pair of alignment lugs 430, each positioned approximately an equal distance on opposite sides of the associated bore axis 112A. The alignment lugs 430 are each preferably cylindrical, with spherical bearing surfaces 440 facing the rear imaging device 120. The support frame 410 extends into a frame recepticle 450 extending into the housing 122H of the rearward imaging device 120 and aligned with the bore axes 112A and 122A. Mounted within the rear wall of the frame recepticle 450 are a pair of female alignment sockets 460 which are engaged by the alignment lugs 430 as the imaging devices 110 and 120 are brought together into the closed position. As is best shown in the detail drawing of FIG. 9A, the alignment sockets 460 have conical inner surfaces, which bear against the cylindrical bearing surfaces of the alignment lugs 430 to align the imaging devices 110 and 120.

Figure 10:
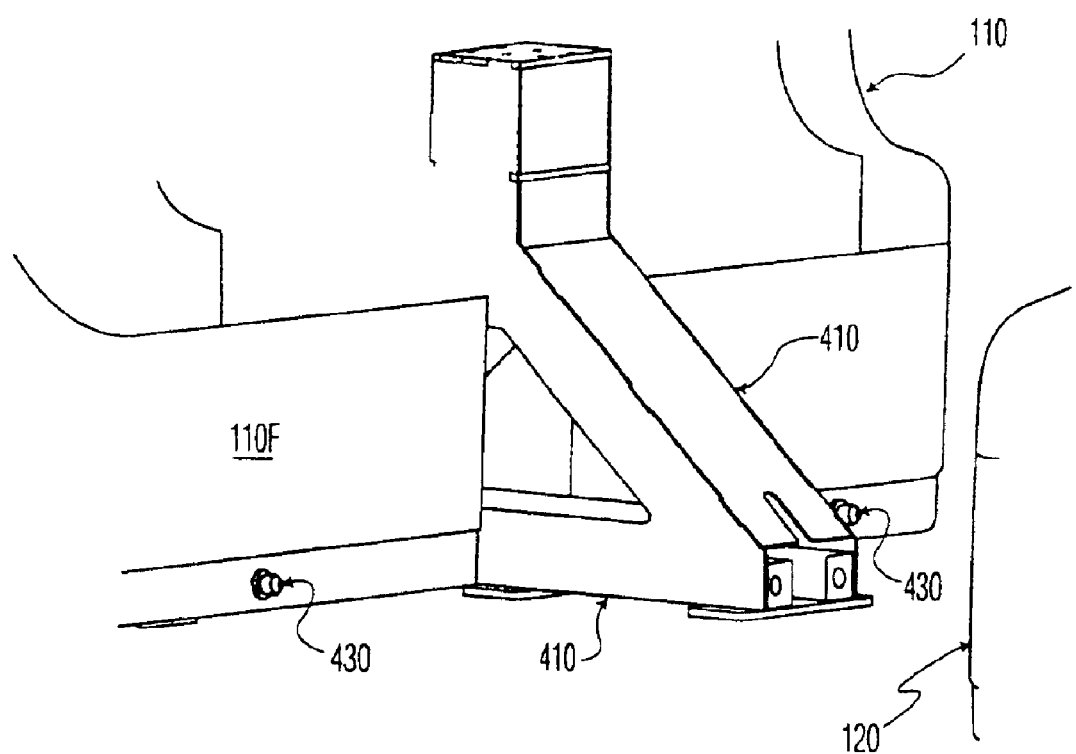
FIG. 10 is a partial perspective view of one of the imaging devices, illustrating alternative structure for aligning the devices in an adjoining position.
Figure 11:
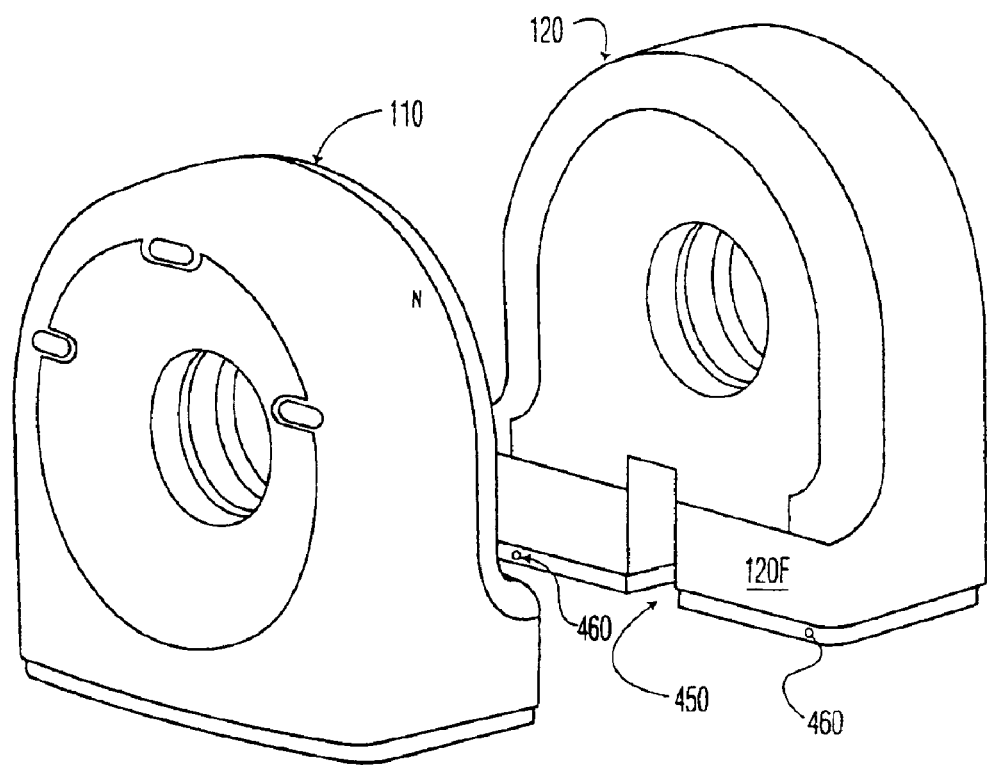
FIG. 11 is a perspective view of two imaging devices, illustrating further the alternative alignment structure shown in FIG. 10.

Referring now to FIGS. 10 and 11, shown is an alternate configuration of the alignment mechanism 400, in which the alignment lugs 430 and their corresponding alignment sockets 460 are mounted at locations adjacent the sides of the respective imaging devices 110 and 120. This configuration may also be combined with the configuration of the alignment mechanism 400 shown in FIGS. 7, 8 and 9.

The support frame 410 also may be utilized as a vertical actuator to vertically position a patient table mounted on the support frame, between the imaging devices 110 and 120, in accordance with U.S. patent application Ser. No. 10/027, 843, entitled "Multimodality Medical Imaging System and Method With Patient Handling Assembly", previously incorporated by reference herein.

Having thus described the present invention by reference to certain of its preferred embodiments, it is noted that the embodiments disclosed are illustrative rather than limiting in nature and that a wide range of variations, modifications, changes, and substitutions are contemplated in the foregoing disclosure and, in some instances, some features of the present invention may be employed without a corresponding use of the other features. Many such variations and modifications may be considered obvious and desirable by those skilled in the art based upon a review of the foregoing description of preferred embodiments. Accordingly, it is appropriate that the appended claims be construed broadly and in a manner consistent with the scope of the invention.

What is claimed is:

1. A medical imaging apparatus, comprising:
a first imaging device for obtaining one or more images of a subject patient, wherein at least a portion of the first imaging device has a first bore through which a patient axially translates during formation of one or more images by the device;
a second imaging device for obtaining one or more images of the subject patient, wherein at least a portion of the second imaging device has a second bore through which a patient axially translates during formation of the images by the device;
the first and second imaging devices, each secured by a housing in a fixed position relative to the other during the formation of one or more images of the subject patient, wherein the bore of each device is substantially aligned axially with the bore of the other; and
an actuating mechanism for moving the first and second imaging devices between an adjoining position, wherein a substantially continuous bore is formed by the first and second bores, and an open position, wherein the first and second bores are separated by a distance sufficient to allow direct access by a caregiver to a subject patient, positioned between the first and second bores.

2. The medical imaging apparatus of claim 1, wherein the first imaging device comprises one of a group consisting of CT, MRI, X-Ray, and Ultrasound devices.

3. The medical imaging apparatus of claim 1, wherein the second imaging device comprises one of a group consisting of SPECT and PET devices.

4. A medical imaging apparatus, comprising:
a first medical imaging device having a first opening for receipt of a subject patient;
a second medical imaging device having a second opening for receipt of the subject patient;
alignment structure securing the openings of the first and second imaging devices in alignment with an imaging axis during the formation of one or more images, by at least one of the imaging devices, of the subject patient;
a patient support structure extending through the openings of the first and second imaging devices during the formation of one or more images by at least one of the imaging devices; and
an actuator for separating the first and second openings of the first and second imaging devices from each other by a selected distance, wherein the distance between the first and second openings is sufficient to allow direct tactile contact between a caregiver and the subject patient.

5. A medical imaging apparatus, comprising:
a first medical imaging device having a first opening for receipt of a subject patient;
a second medical imaging device having a second opening for receipt of the subject patient;
alignment structure securing the openings of the first and second imaging devices in alignment with an imaging axis during the formation of one or more images, by at least one of the imaging devices, of the subject patient;
a patient support structure extending through the openings of the first and second imaging devices during the formation of one or more images by at least one of the imaging devices; and
an actuator for separating the first and second openings of the first and second imaging devices from each other by a selected distance, wherein the axes of the first and second openings of the first and second imaging devices are substantially aligned.

6. The medical imaging apparatus of claim 5, wherein the alignment structure comprises a lug mounted on the first imaging device engaging socket mounted on the second imaging device.

7. A medical imaging apparatus, comprising:

a first housing supporting a first tomographic scanner having a first bore for obtaining tomographic imaging information from at least a portion of a patient;

a second housing supporting a second tomographic scanner having a bore for obtaining tomographic imaging information from at least a portion of a patient;

an alignment structure securing the bores of the first and second imaging devices in alignment with an imaging axis during the formation of one or more tomographic images, by at least one of the imaging devices, of the subject patient wherein the alignment structure comprises a lug mounted on the first imaging device engaging a socket mounted on the second imaging device; and a linear actuator for positioning each of the first and second housings between an adjoined position, with the axes of the first and second scanner bores substantially aligned, and a separated position, with the scanner bores spaced from each other by the linear actuator.

8. The medical imaging apparatus of claim 7, wherein the first and second housings form a patient access area between the first and second scanners bores when placed in the adjoining position, the access area allowing direct access by a caregiver to a patient extending through the first scanner bore and at least partially positioned between the first and second scanners.

9. The medical imaging apparatus of claim 7, wherein the linear actuator comprises:

a guide rail substantially aligned with the axes of the first and second bores; and a drive assembly for moving at least one of the first and second housings relative to the other housing in a direction substantially aligned with the axes of the first and second bores.

10. The medical imaging apparatus of claim 7, wherein the first and second scanners are adapted to operate in different modalities with respect to each other.

11. The medical imaging apparatus of claim 10, wherein one of the first and second scanners is adapted to obtain imaging information representing anatomical structures of the patient.

12. The medical imaging apparatus of claim 10 or 11, wherein one of the first and second scanners is adapted to obtain imaging information representing physiologic functions of the patient.

13. A medical imaging apparatus, comprising:

a first medical imaging device having a first opening for receipt of a subject patient;

a second medical imaging device having a second opening for receipt of the subject patient;

alignment structure securing the openings of the first and second imaging devices in alignment with an imaging axis during the formation of one or more images, by at least one of the imaging devices, of the subject patient;

a patient support structure extending through the openings of the first and second imaging devices during the formation of one or more images by at least one of the imaging devices; and an actuator for separating the first and second openings of the first and second imaging devices from each other by a selected distance, wherein the distance between the first and second openings is sufficient to allow a caregiver to perform one or more interventional applications on the subject patient, wherein at least one of said one or more interventional applications is a portion of a biopsy procedure.

14. A medical imaging method, comprising the steps of:

operating a first medical imaging device having a first operating modality to obtain a first set of imaging information from at least a portion of a subject of interest;

operating a second medical imaging device having a second operating modality to obtain a second set of imaging information from at least a portion of the subject of interest; and configuring an arrangement of the first medical imaging device and the second medical imaging device, said configuring including actuating an actuator to move at least one of the first medical imaging device or the second medical imaging device such that the first medical imaging device and the second medical imaging device are in a first configuration;

wherein the first configuration includes the first medical imaging device and the second medical imaging device positioned in a substantially adjoining position.

15. The medical imaging method of claim 14, further comprising the step of:

configuring an arrangement of the first medical imaging device and the second medical imaging device, said configuring including actuating an actuator to move at least one of the first medical imaging device or the second medical imaging device such that the first medical imaging device and the second medical imaging device are in a second configuration;

wherein the second configuration includes the first medical imaging device and the second medical imaging device positioned in a substantially separated position to allow a caregiver to perform at least a portion of an interventional procedure on the subject of interest.

* * * * *